United States Patent [19]

Itoh

[11] Patent Number: 5,523,504

[45] Date of Patent: Jun. 4, 1996

[54] PROCESS FOR MANUFACTURING ALKENYL AROMATIC COMPOUNDS

[75] Inventor: Takashi Itoh, Satte, Japan

[73] Assignees: Cosmo Oil Co., Ltd.; Petroleum Energy Center, both of Tokyo, Japan

[21] Appl. No.: 306,609

[22] Filed: Sep. 15, 1994

[30] Foreign Application Priority Data

| Sep. 17, 1993 | [JP] | Japan | 5-255081 |
| May 7, 1994 | [JP] | Japan | 6-117532 |
| Aug. 23, 1994 | [JP] | Japan | 6-221004 |

[51] Int. Cl.$^6$ ........................................ C07C 2/66
[52] U.S. Cl. ........................ 585/452; 585/438; 585/467
[58] Field of Search ........................ 585/438, 452, 585/455, 467

[56] References Cited

U.S. PATENT DOCUMENTS 5,329,058  7/1994  Shimada ........................ 585/452

*Primary Examiner*—Ponnathapura Achutamurthy
*Attorney, Agent, or Firm*—Oblon, Spivak, McClelland, Maier & Neustadt

[57] ABSTRACT

A process for manufacturing an alkenyl aromatic compound which is an industrially valuable compound as a raw material for the manufacture of naphthalenedicarboxylic acid, a highly useful raw material of polymers. The process comprises reacting an alkylbenzene and 1,3-butadiene in the presence of (a) metallic sodium, (b) at least one compound selected from the group consisting of salts of potassium, salts of rubidium, and salts of an alkaline earth metal, and (c) an aromatic compound capable of producing a charge-transfer complex together with metallic sodium. High purity alkenyl aromatic compound can be manufactured at a high yield using a simple procedure.

10 Claims, 1 Drawing Sheet

PROCESS FOR MANUFACTURING ALKENYL AROMATIC COMPOUNDS

BACKGROUND OF THE INVENTION

1. Field of the Invention

The present invention relates to a process for manufacturing an alkenylaromatic compound which is an industrially valuable compound as a raw material for the manufacture of naphthalenedicarboxylic acid, a highly useful raw material of polymers such as polyethylene naphthalate (PEN).

2. Description of the Background Art

In the process for manufacturing alkenyl aromatic compounds, an alkylbenzene and 1,3-butadiene are reacted in the presence of an alkali metal as a catalyst. Conventionally known catalysts used in this reaction are metallic potassium (Japanese Patent Publication (kokoku) No. 17973/1975) and a combination of metallic potassium and metallic sodium (Japanese Patent Publication (kokoku) Nos. 34570/1981, 26489/1982, and 17973/1975).

Conventional methods using these catalysts, however, have the following drawbacks.

(1) High production cost due to the use of expensive metallic potassium.

(2) Risks associated with the use of metallic potassium. Metallic potassium is highly reactive with water, moist air, and the like, and is thus ignited by merely brought to come into contact with them. Thus, it may fire combustible materials, such as raw materials and reaction products. Therefore, using metallic potassium as it is is very dangerous.

In an effort of avoiding the use of metallic potassium, a method of using metallic sodium and an inorganic salt of potassium has been proposed (Japanese Patent Laid-open (kokai) Nos. 31935/1972, 226927/1992, and WO 91-16284).

This method does not necessarily provide industrial advantage, because of (3) requirement for special agitators, such as an emulsification apparatus, and for the use of high purity inorganic salt of potassium.

An object of the present invention is therefore to provide a process for manufacturing an alkenyl aromatic compound from an alkylbenzene and 1,3-butadiene, which is free from all the problems (1)–(3) above.

As a result of extensive studies for achieving this object, the present inventor has found that the combined use of (a) metallic sodium, (b) a salt of potassium, rubidium, or an alkaline earth metal, in place of metallic potassium, and (c) an aromatic compound capable of producing a charge-transfer complex together with metallic sodium ensures reducing the amount of metallic sodium and increasing the yield of the alkenyl aromatic compound by the reaction of alkylbenzene and 1,3-butadiene by using only a simple agitator.

SUMMARY OF THE INVENTION

Accordingly an object of the present invention is to provide a process for manufacturing an alkenyl aromatic compound which comprises reacting an alkylbenzene and 1,3-butadiene in the presence of:

(a) metallic sodium, (b) at least one compound selected from the group consisting of salts of potassium, salts of rubidium, and salts of an alkaline earth metal, and (c) an aromatic compound capable of producing a charge-transfer complex together with metallic sodium.

Other and further objects, features and advantages of the present invention will appear more fully from the following description.

DETAILED DESCRIPTION OF THE INVENTION AND PREFERRED EMBODIMENTS

Figure 1:
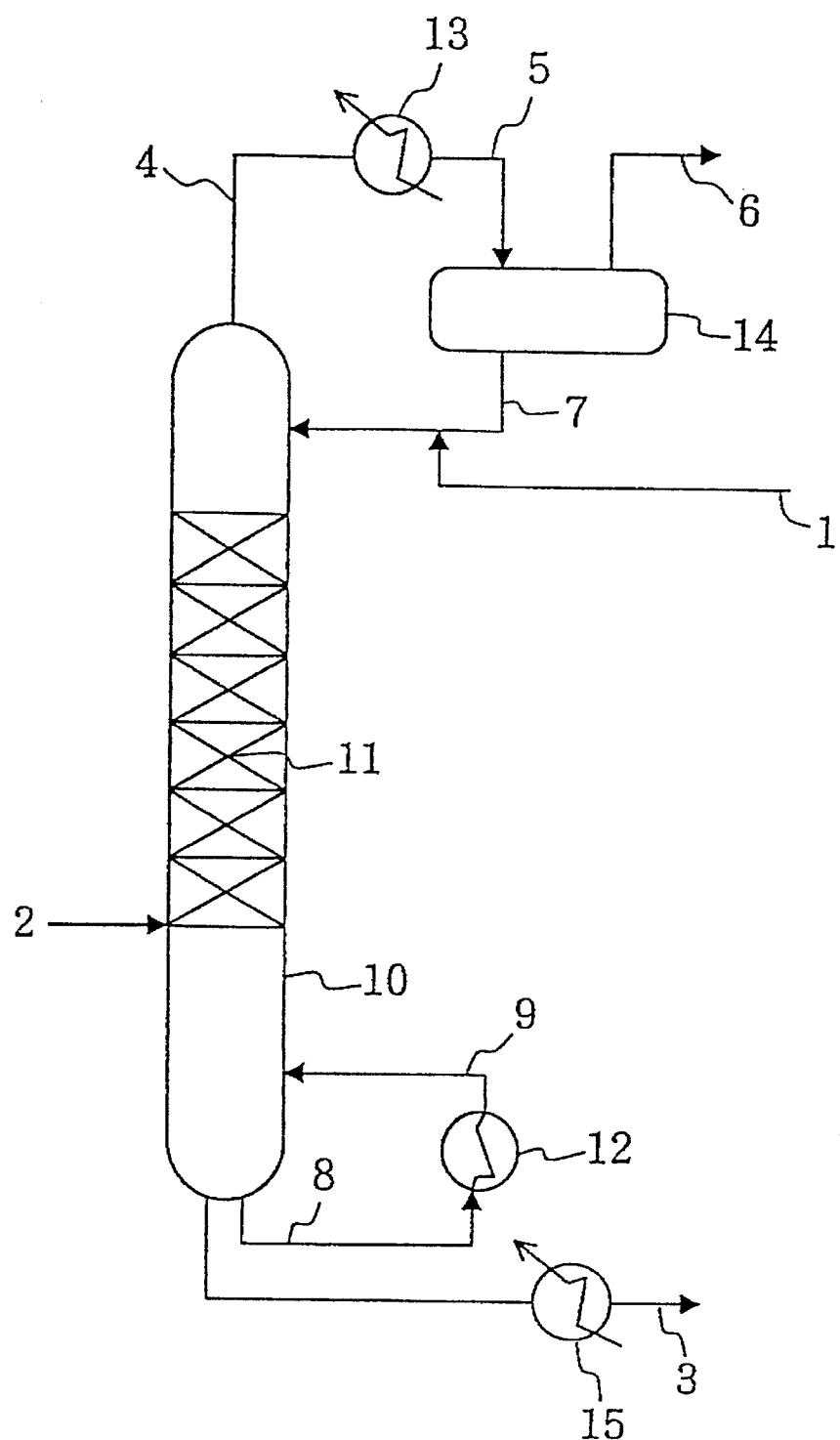
FIG. 1 is a drawing illustrating one embodiment of the device for carrying out the process of the present invention.

The alkylbenzene in the present invention denotes a compound having 1 or 2 groups selected from methyl group and ethyl group on benzene ring. Toluene, ethylbenzene, o-xylene, m-xylene, and p-xylene are given as specific examples.

It is desirable that one of these alkylbenzenes be used alone. If two or more of them are used together, it is difficult to separate each target compound at a high purity from alkenyl aromatic compounds produced by the reaction.

Further, it is desirable for the purpose of effective isolation of target compound to use an alkylbenzene with a purity as high as possible. A specific desirable purity is 95% or higher, and especially 98% or higher.

Notwithstanding this stringent purity requirement for alkylbenzene, inclusion of a slight amount of hydrocarbons having no alkyl groups, such as benzene and cyclohexane, is acceptable.

Alkylbenzene with a water content as low as possible is preferred, because the water impairs the catalyst by reducing the activity of metallic sodium. A preferred water content is below the detectable sensitivity by Karl Fischer's method which is a common measuring method of a water content, and specifically it is below several ppm.

The use of dehydrated alkylbenzene is therefore preferred.

The method for dehydrating alkylbenzenes which can be employed include a method of absorbing and separating water using an appropriate drying agent such as activated alumina, silica gel, molecular sieve, or activated carbon; a low temperature separation method; and a method of contacting alkylbenzenes and metallic sodium or metallic potassium. Among these, the last-mentioned method, i.e. the method of contacting alkylbenzenes and metallic sodium or metallic potassium, is preferred.

There are no limitations as to the method by which 1,3-butadiene to be reacted with alkylbenzene is manufactured. There is also no need for the purity of the 1,3-butadiene to be as high as the above-mentioned purity of alkylbenzene. The reaction proceeds smoothly and there are no needs for isolation of the target compound irrespective of the purity of 1,3-butadiene. Crude butadiene obtained, for example, by the dehydrogenation of butane or butene can be used as is, or 1,3-butadiene obtained by purification of this crude butadiene by extraction or the like can be also used.

Nevertheless, a lower water content of 1,3-butadiene is more desirable from the same reasons as mentioned above in connection alkylbenzenes. Specifically, a preferred water content of 1,3-butadiene is several ppm. Thus, the use of dehydrated 1,3-butadiene is preferred.

The method for dehydrating 1,3-butadiene which can be employed include a method of absorbing and separating water using an appropriate drying agent such as activated alumina, silica gel, molecular sieve, or activated carbon; and a low temperature separation method.

The catalyst for the reaction of alkylbenzene and 1,3-butadiene comprises (a) metallic sodium, (b) a salt of potassium, rubidium, or an alkaline earth metal, and (c) an aromatic compound capable of producing a charge-transfer complex together with metallic sodium. It is preferable to use a dispersion of metallic sodium (component (a)) and said salt of potassium, rubidium, or an alkaline earth metal (component (b)).

Metallic sodium with a high purity is preferred, although it may contain a slight amount of calcium, magnesium, and potassium. The purity of 90% or higher, especially 99.0% or higher, is preferred.

Given as specific examples of the salt, which is component (b) of the catalyst, are potassium oxide, potassium hydroxide, potassium carbonate, potassium sulfate, potassium chloride, potassium aluminate, rubidium oxide, rubidium hydroxide, rubidium carbonate, rubidium sulfate, calcium oxide, calcium hydroxide, calcium carbonate, calcium sulfate, magnesium oxide, magnesium hydroxide, magnesium carbonate, magnesium sulfate, and the like. These salts may be used either alone or in combination of two or more. Among these, preferred salts are potassium hydroxide, potassium carbonate, potassium oxide, rubidium hydroxide, rubidium carbonate, rubidium oxide, calcium hydroxide, calcium carbonate, calcium oxide, magnesium hydroxide, magnesium carbonate, and magnesium oxide.

These salts used as component (b) of the catalyst may contain sodium salts, such as sodium carbonate and sodium chloride, at a weight ratio of component (b):sodium salts of about 10:1 to 1:10, preferably about 10:1 to 1:1. Inclusion of sodium salts in the salts of component (b) may occasionally promote the function of the catalyst used in the process of the present invention.

These salts of component (b) (hereinafter "the salts" denotes component (b) which may contain sodium salts) should be sufficiently dry. In particular, it is preferable that these salts be sufficiently calcined at a high temperature of 200° to 600° C. in order to adequately promote their activity. Further, the salts of component (b) are preferably particles with a mean diameter of 100 μm or smaller, particularly 10 to 50 μm. Adjustment of the particle size can be carried out by sieve or the like.

Although there are no specific limitations to the ratio of metallic sodium and the salts of component (b) when metallic sodium is dispersed in the salts, the amount of metallic sodium is adjusted to make its final content in the catalyst 0.1 to 30% by weight, preferably 0.5 to 20% by weight, and particularly preferably 1 to 10% by weight. If the amount of metallic sodium is smaller than 0.1 by weight, the action of the catalyst in the present invention is insufficient. The amount of metallic sodium greater than 30% by weight brings about no catalytic effects proportionate to the added amount, and only makes the process uneconomical.

A typical method of dispersing metallic sodium in the salts comprises dispersing metallic sodium in the salts and supporting the former in the latter. The dispersion-supporting is preferably carried out in an inert solvent. The master batch method is employed for homogeneously supporting 0.1–30% weight of metallic sodium on the salts by dispersion-supporting in an inert solvent. Another method is preparing suspensions each containing one of the components.

For example, in the case where 3% by weight of metallic sodium is dispersed in the salt, 3 parts by weight of metallic sodium and 97 parts by weight of the salt are together put into 1333 parts by weight of a solvent (alkylbenzene) and the mixture is stirred at a high speed at 110°–130° C. Alternatively, a suspension containing metallic sodium and the salt at a suitable ratio is prepared in advance, and this suspension is further dispersed by the remaining salts in the solvent (alkylbenzene).

Another method for the dispersion-supporting is mixing a suspension of 3 parts by weight of metallic sodium in 333 parts by weight of alkylbenzene and a suspension of 97 parts by weight of the salts in 1000 parts by weight of alkylbenzene.

Still another method is preparing a suspension of 3 parts by weight of metallic sodium and 47 parts by weight of the salt in 500 parts by weight of alkylbenzene and another suspension of 50 parts by weight of the salts in 833 parts by weight of alkylbenzene, and then mixing the two suspensions.

Even if the solvent (alkylbenzene) is not used, a homogeneous catalyst exhibiting superior activity and selectivity can be prepared by the master batch method and the dispersion-supporting using an inert solvent.

In the industrial application of the inert solvent dispersion-supporting method, the same alkylbenzene as the raw material is preferably used as the solvent.

When the dispersion of metallic sodium and the salt is desired to be held fixed, such as the case where the reaction-distillation as hereinafter described is carried out, a molded catalyst made from a porous material with metallic sodium and the salt supported thereon can be used.

Given as examples of porous materials for holding the catalyst, are alumina, silica, silica alumina, X- and Y-zeolite, mordenite, pentasyl zeolite such as ZSM-5, L-zeolite, ion-exchanged resin, and naturally occurring clay minerals such as montmollilonite and sepiolite.

When these porous materials are a salt themselves, such as potassium ion-exchanged X-zeolite or Y-zeolite, which are faujasite zeolite, potassium ion-exchanged zeolite of mordenite, potassium ion-exchanged L-zeolite, potassium ion-exchanged resin, as well as rubidium-, calcium-, or magnesium-ion-exchanged type of these porous materials, there are no need for the catalyst to separately contain the aforementioned salts as component (b). Accordingly, these porous materials which are salts themselves (hereinafter called "porous salts") are included in the salts as component (b).

One of the methods employed for supporting metallic sodium and the salts on a porous material comprises molding the salts, calcined in advance to a degree where there is no substantial amount of water contained therein, alone when the salt is a porous material or together with the porous material when the salt is not a porous material, to produce molded particles with a particle size of 1.6 mm (⅛") or larger, followed by calcining the molded particles at 200°–500° C. In this instance, when molded particles in the shape of a ring, a saddle, or the like are desired, a molding binder, such as silica sol or alumina sol, can be used. As the molding method, tablet method, casting method, extrusion, or the like can be used with no specific limitations.

The particle size is not necessarily limited to 1.6 mm or larger. It is possible to use smaller size particles, e.g. of a size smaller 1.6 mm and larger than 0.1 mm, provided that in order to avoid decrease in the fractionation distillation efficiency due to pressure loss caused by the small size particles these are desirably used filled in mesh containers, such as containers made from cloth, metallic wires, glasses fibers, polymer fibers, or the like. These types of containers are disclosed in U.S. Pat. No. 4,232,530, U.S. Pat. No. 4,242,530, U.S. Pat. No. 4,250,052, U.S. Pat. No. 4,302,356, and U.S. Pat. No. 4,307,251.

In order for metallic sodium to be carried on the calcined dry material, there is employed a dry method which comprises causing metallic sodium, melted at 65° to 700° C., preferably at 100° to 600° C., and more preferably at 200° to 500° C., in a saturated dehydrated carrier gas inert to the metallic sodium, such as nitrogen, hydrogen, helium, or argon, to come into contact with the calcined dry material, or a wet method causing the melted metallic sodium as is or dispersed in an inert solvent to come into contact with the calcined dry material. Normal paraffins having 8–16 carbon atoms, alkylbenzenes, alkylnaphthalenes, or the like can be used as the solvent in the wet method. The contact temperature in the wet method is preferably above the melting point of metallic sodium (97.8° C.) and below the boiling point of the solvent.

The catalyst with voids of 20 to 65 vol %, particularly 30 to 60 vol %, is preferably used in the process of the present invention.

Given as examples of aromatic compounds capable of producing a charge-transfer complex together with metallic sodium, which is component (c) in the catalyst of the present invention, are condensed aromatic compounds, such as naphthalene, anthracene, phenanthrene, pyrene, perylene, pentacene, coronene, quinone, benzoquinone, anthraquinone, cyclophane, graphite, and fullerene ($C_{60}$, $C_{70}$); polycyclic aromatic compounds, such as triphenylene and tetraphenylene; cyano-, nitro-, or halogeno-substituted compounds of these; as well as cyanobenzene, dicyanobenzene, tetracyanobenzene, nitrobenzene, trinitrobenzene, dichlorotetracyanobenzene, tetracyanoquinodimethane, dichloroquinone, tetracyanoquinone, and the like.

These aromatic compounds may be used at any proportion to the dispersed and supported catalyst components. If the amount is too small, the intended effects will not be exhibited; if too large, no catalytic effects proportionate to the added amount will not be obtained, only making the process uneconomical. A suitable amount of aromatic compounds is 0.001 to 50 mols, preferably 0.01 to 10 mols, and particularly preferably 0.05 to 2 mols, for one mol of metallic sodium.

The timing at which the aromatic compounds is added to the dispersion mixture comprising metallic sodium and the salt may be either prior to or after the addition of the metallic sodium in the process of making the above-described dispersion consisting of the metallic sodium and the salts, or after the preparation of this dispersion. In view of assuring dispersibility of metallic sodium, the addition after the preparation of the dispersion of metallic sodium and the salts is preferred.

The activity of the catalyst comprising metallic sodium, said salt, and the aromatic compound capable of producing a charge-transfer complex together with metallic sodium thus prepared is improved by subjecting a mixture of this catalyst and alkylbenzene to a pretreatment at 100° to 200° C. for 0.1 to 5 hours before the catalyst is used for the reaction of 1,3-butadiene and the alkylbenzene.

The molar ratio of alkylbenzene and 1,3-butadiene used in the reaction is suitably selected from the normal range; e.g., the approximate ratio of alkylbenzene: 1,3-butadiene may be 1:0.001 to 1:0.5, preferably 1:0.01 to 1:0.4, and more preferably 1:0.05 to 1:0.3. The amount of alkylbenzene used for the above-described dispersion treatment of metallic sodium in the salts is accounted for this ratio of alkylbenzene and 1,3-butadiene.

The amount of the catalyst comprising (a) metallic sodium, (b) said salt, and (c) said aromatic compound capable of producing a charge-transfer complex together with metallic sodium used in this reaction is 0.01 to 50 parts by weight, preferably 0.05 to 30 parts by weight, and particularly preferably 0.1 to 10 parts by weight, for 100 parts by weight of alkylbenzene.

It is desirable that the reaction of alkylbenzene and 1,3-butadiene in the process of the present invention be carried out substantially in the absence of water and oxygen. Water may convert metallic sodium into sodium hydroxide, resulting in decrease in its catalytic activity, and oxygen may deactivate the catalyst which forms a charge-transfer complex.

Therefore, the raw materials to be charged to the reaction system, i.e. alkylbenzene and 1,3-butadiene, are desirably those dehydrated.

Further, in order to avoid the presence of substantial amount of oxygen and water in the open spaces of the reaction system, it is desirable to fill the open spaces with dry inert gas, such as dry nitrogen or dry argon, or with the vapor of alkylbenzene or the like, when the reaction is carried out under pressurized reaction conditions above the boiling point of the alkylbenzene.

The reaction temperature in the process of the present invention is preferably about 50° to 200° C. If the temperature is lower than 50° C., by-products may be produced or it takes a longer period of time for the reaction. If it is higher than 200° C., production of the other by-products may increase. The reaction temperature from 80° C. to 180° C. is preferred.

The reaction time in the range of 0.05 to 10 hours is preferably applicable. The reaction time is dependent on the amount of the catalyst (g-catalyst), the composition of the catalyst (g-metallic sodium, g-salt, g-aromatic compound capable of producing a charge-transfer complex together with metallic sodium), the reaction temperature (°C.), the molar ratio of alkylbenzene and 1,3-butadiene (g-alkylbenzene/g-1,3-butadiene), the method of reaction, and the like. An appropriate reaction time is determined taking the purity of the target compounds, the manner in which the catalyst is used (e.g. adoption of catalyst recycle), and the like into consideration.

Generally, the reaction time is longer as the values for these factors decrease. The preferable reaction time is 0.1 to 8 hours, and particularly 0.3 to 5 hours.

Any reaction methods may be employed for the reaction in the process of the present invention. Such reaction methods include batch reaction in which the raw materials (alkylbenzene and 1,3-butadiene) and the catalyst comprising metallic sodium, the salt, and the aromatic compound capable of producing a charge-transfer complex together with metallic sodium are charged altogether and reacted; semi-batch reaction in which alkylbenzene and the catalyst is first charged to the reactor and 1,3-butadiene is added as the reaction proceeds; continuous reaction in which alkylbenzene, 1,3-butadiene, and the catalyst are continuously charged to the reactor; and the reaction-distillation method in which alkylbenzene and 1,3-butadiene are introduced to the upper and lower parts, respectively, of a reactor column filled with the catalyst, and the target-reaction products flow down to the bottom (FIG. 1). Any suitable combinations of these methods can be also employed. Among these, the semi-batch reaction, the continuous reaction, or the reaction-distillation method are preferred, in order to suppress production of by-products such as two or more mols of 1,3-butadiene addition compounds.

There are two types for the method of continuous reaction. One is the method of feeding alkylbenzene continuously to the fixed catalyst bed, while introducing 1,3-butadiene to the alkylbenzene. The other method is effecting reaction while dispersing the catalyst with stirring in the reaction system consisting of alkylbenzene and 1,3-butadiene.

Any types of reactors, such as tubular-type, column-type, and vessel-type reactors, may be used for the continuous reaction.

One of the preferred manners of carrying out the continuous reaction is the crossing-flow type reaction method in which a plural number of reaction zones are provided and 1,3-butadiene is quantitatively fed to each reaction zone.

There are no specific limitations as to the reaction procedure inasmuch as alkylbenzene and 1,3-butadiene are sufficiently mixed and caused to come into contact with the catalyst, provided that in the case where 1,3-butadiene is introduced to the reaction system in which the catalyst is present, it is desirable to introduce alkylbenzene and 1,3-butadiene as a mixture, for example, as a liquid mixture consisting of liquid alkylbenzene and liquid 1,3-butadiene or as a vapor-liquid mixture consisting of gaseous 1,3-butadiene and liquid alkylbenzene. This is to prevent 1,3-butadiene from being choked up with inlet port due to attachment of rubber-like or resinous substance which are considered to be polymers of 1,3-butadiene. An alternative method of avoiding the choke-up is supplying 1,3-butadiene directly to the space where the reaction is taking place so as to ensure absorption and reaction of the 1,3-butadiene on the surface of reactants in which the catalyst is present.

Further, it is possible to introduce 1,3-butadiene by injection carried on a carrier gas. Injection can also provide the effect of agitation. An inert gas from which oxygen and water have been removed, such as nitrogen, argon, or hydrogen, is preferably used here.

This reaction is preferably carried out under agitation. Introduction of gaseous 1,3-butadiene may provide the effect of agitation. The degree of agitation should be sufficient for homogeneously dispersing the catalyst throughout the reactor and for homogeneously mixing the raw materials and the products.

When the reaction is carried out in a liquid phase dispersion reaction system, the used catalyst may be separated by a known method, such as centrifugal precipitation, gravity precipitation, solid phase separation from a liquid-solid mixture at a low temperature (e.g. filtration, centrifuge), or the like. The catalyst recovered can be recycled for reuse.

When the catalyst is deactivated and loses the catalytic activities, the catalyst is covered by sodium hydroxide which has no catalytic activity. Such a catalyst is oxidized and calcined to burn the organic substances attached thereto and to convert sodium hydroxide into sodium carbonate, following which the catalyst is regenerated for reuse by the addition of metallic sodium and the aromatic compound capable of producing a charge-transfer complex together with metallic sodium.

In the reaction-distillation method, the reaction time may be longer than the above-described reaction time, because it is difficult for two or more mols of 1,3-butadiene adduct to alkylbenzene, which is one type of the by-products, to be produced by the reaction-distillation method. The reaction time in the reaction-distillation method can be determined chiefly from the feed rate of 1,3-butadiene and the catalyst fill length of the column.

The reaction-distillation method is then illustrated in detail referring to FIG. 1.

In FIG. 1, the catalyst is filled in the part 11 of the distillation column 10. The raw material alkylbenzene is supplied via line 1. This fresh alkylbenzene is combined with the unreacted alkylbenzene, which flows out from line 4 at the top of the column as effluent, is condensed in condenser 13, and sent via line 5 to vapor-liquid separator 14, where it is separated from unreacted 1,3-butadiene, which is drawn out from line 6. The alkylbenzene is then fed to column 10 from the top.

On the other hand, 1,3-butadiene is charged via line 2 to the lowest part of catalyst-fill section 11 of column 10 in gaseous or liquid state and caused to come into contact with alkylbenzene while it moves up to the top of the column, thereby producing an alkenyl aromatic compound.

Because the alkenyl aromatic compound produced has a boiling point higher than both alkylbenzene and 1,3-butadiene, it is liquid at temperatures at which alkylbenzene and 1,3-butadiene are present together in a state of vapor or liquid. Thus, almost all alkenyl aromatic compound flows down to the bottom of the column.

This bottom product is drawn out from line 8 and sent to reboiler 12, where it is heated above the temperature at which the alkylbenzene is completely vaporized, but lower than the temperature at which all of the target alkenyl aromatic compound is vaporized, and sent back to reaction-distillation column 10 via line 9. The other portion of the column bottom product is cooled in cooler 15 and collected as the alkenyl aromatic compound product via line 3.

Because the product from this reaction system once separated has no chance of coming into contact with 1,3-butadiene as in the case of the batch reaction system, the fluid collected via line 3 consists only of alkenyl aromatic compound which does not substantially contain unreacted alkylbenzene or by-produced di- or more substituents.

The aromatic compound capable of producing a charge-transfer complex together with metallic sodium used in the process of the present invention is considered to exhibit an action of reducing the activation energy required for the production of alkenyl aromatic compounds. This action contributes to the reduction of agitation energy and the amount of the catalyst used for the reaction of alkylbenzene and 1,3-butadiene to produce alkenyl aromatic compounds.

Further, the use of the dispersion of metallic sodium and the salts not only increases the area in which the metallic sodium comes into contact with the reactants, but also ionizes a portion of the salts, thereby discharging ion into the reaction system, or produces complexes consisting of all components, including raw materials (alkylbenzene and 1,3-butadiene), the metallic sodium, the salts, and the aromatic compound capable of producing a charge-transfer complex together with metallic sodium. All of these are considered to reduce activation reaction as compared with the reaction in which metallic sodium is used alone.

According to the process of the present invention, 5-phenylpentene is synthesized from toluene; 5-(o-tolyl)pentene from o-xylene; 5-(p-tolyl)pentene from p-xylene; 5-(m-tolyl)pentene from m-xylene; and 5-(phenyl)hexene from ethylbenzene.

The process of the present invention exhibits the following effects.

(1) A highly active and selective alkenylation reaction can proceed with a simple operation consisting only of gentle agitation. The production of unwanted side reaction products which are difficult to separate from the target compound can be therefore suppressed, Thus, a high purity target product can be obtained at a high yield.

(2) The catalyst components used are inexpensive, safe, free from any danger, and readily separable from the reaction mixture. There are no need for the use of components such as metallic sodium-potassium alloy which is expensive, has a risk of being ignited, and is difficult to separate from the reaction mixture.

Japanese Patent Application No. 255081/1993 filed on Sep. 17, 1993 and No. 117532/1994 filed on Jul. 5, 1994, and another Japanese Patent Application filed on Aug. 23, 1994 are herein incorporated as references.

Other features of the invention will become apparent in the course of the following description of the exemplary embodiments which are given for illustration of the invention and are not intended to be limiting thereof.

EXAMPLES

Example 1

50 parts by weight of anhydrous o-xylene and 0.45 part by weight of metallic sodium (purity: 99.95%) were charged under a nitrogen atmosphere to a 500 ml three-necked flask equipped with a stirrer, a nitrogen inlet tube, 1,3-butadiene inlet tube, a condenser tube, and calcium chloride tube. The mixture was stirred by a mechanical stirrer at 120° C. to make the metallic sodium into fine particles.

Separately a dispersion of potassium carbonate was prepared by adding 50 parts by weight of o-xylene to 15 parts by weight of potassium carbonate (pulverized to an average particle size of 50 μm and calcined at 600° C. for 5 hours) and stirring the mixture at 100° C.

This dispersion of potassium carbonate was charged to said dispersion of fine particulate metallic sodium, and the mixture was stirred at a high speed for 10 minutes. Next, anthraquinone, as the aromatic compound capable of producing a charge-transfer complex together with metallic sodium, in an amount of 4.8 mol % of the metallic sodium, and 100 parts by weight of o-xylene were added, followed by stirring at a high speed for one hour at 140° C.

Then, 1,3-butadiene was introduced to the mixture at a flow rate of 27.5 ml/min at 140° C. for 2 hours.

The reaction mixture was cooled to 100° C. immediately after the reaction to separate the catalyst from the reaction solution. After washing with water, the excess amount of o-xylene was evaporated, and the residue was distilled under reduced pressure to obtain 5-(o-tolyl)pentene. The yield and purity of the 5-(o-tolyl)pentene was measured, and the results are shown in Table 1.

Example 2

200 parts by weight of low water content o-xylene, 15 parts by weight of potassium carbonate (pulverized to an average particle size of 50 μm and calcined at 600° C. for 5 hours), 0.0625 part by weight of naphthalene, and 0.23 part by weight of metallic sodium (purity: 99.95%) were charged under a nitrogen atmosphere to a 500 ml three-necked flask equipped with a stirrer, a nitrogen inlet tube, 1,3-butadiene inlet tube, a condenser tube, and calcium chloride inlet tube. The mixture was stirred at 140° C. for one hour to pulverize the metallic sodium into fine particles. Then, 1,3-butadiene was introduced to the mixture at a flow rate of 27.5 ml/min at 140° C. for two hours.

The reaction mixture was cooled to 100° C. immediately after the reaction to separate the catalyst from the reaction solution. After washing with distilled water, the excess amount of o-xylene was evaporated, the residue was distilled under reduced pressure to obtain 5-(o-tolyl)pentene (purity: 99%) at an yield of 87%.

Example 3–27, Comparative Example 1–3

5-(o-tolyl)pentene was prepared in the same manner as in Example 2, except that the catalyst compositions shown in Tables 1–3 were used. The yield and purity of the 5-(o-tolyl)pentene in each Example and Comparative Example were measured, and the results are shown in Tables 1–3.

As can be understood from Tables 1–3, high purity 5-(o-tolyl)pentene can be prepared at a high yield by the process of the present invention.

In experiments carried out in the same manner as in Example 1, except for using p-xylene instead of o-xylene, 5-(p-tolyl)pentene was obtained with a purity and at an yield as high as the purity and yield of 5-(o-tolyl)pentene.

In Tables 1–3 below, the amounts of Na and salts are indicated as percent by weight of alkylbenzene, and the amount of aromatic compounds capable of producing a charge-transfer complex together with Na is indicated as the mol % for Na.

TABLE 1

| | | Catalyst composition | | Product | |
|---|---|---|---|---|---|
| Example | Na | Salt | Aromatic compound producing a charge-transfer complex with Na | Yield (%) | Purity (%) |
| 1 | 0.23 | K$_2$CO$_3$ 7.5 | Anthraquinone 4.8 | 90 | 99 |
| 2 | 0.11 | K$_2$CO$_3$ 7.5 | Naphthalene 4.9 | 87 | 99 |
| 3 | 0.23 | K$_2$CO$_3$ 7.5 | Anthracene 5.6 | 91 | 99 |
| 4 | 0.23 | KOH 4.0 Na$_2$CO$_3$ 2.0 | Phenanthrene 5.6 | 90 | 99 |
| 5 | 0.23 | K$_2$CO$_3$ 7.5 | Perylene 4.0 | 85 | 99 |
| 6 | 0.23 | K$_2$CO$_3$ 5.0 K$_2$O 2.5 | Cyanobenzene 2.0 | 85 | 98 |
| 7 | 0.23 | K$_2$CO$_3$ 6.0 Na$_2$CO$_3$ 1.0 KCl 0.5 | Tetracyanobenzene 5.6 | 89 | 99 |
| 8 | 0.23 | K$_2$CO$_3$ 7.5 | Dichloroquinone 5.7 | 86 | 98 |
| 9 | 0.23 | K$_2$CO$_3$ 7.5 | Tetracyanoquinone 4.8 | 87 | 99 |
| 10 | 0.45 | K$_2$CO$_3$ 7.5 | Quinoline 15.5 | 45 | 99 |
| Comp. Example 1 | 0.23 | K$_2$CO$_3$ 7.5 | | 1 | 98 |

TABLE 2

| | Catalyst composition | | Product | |
|---|---|---|---|---|
| Example | Na | Salt | Aromatic compound producing a charge-transfer complex with Na | Yield (%) | Purity (%) |
|---|---|---|---|---|---|
| 11 | 0.23 | Rb$_3$CO$_3$ 7.5 | Anthraquinone 4.8 | 90 | 98 |
| 12 | 0.23 | Rb$_3$CO$_3$ 7.5 | Naphthalene 7.8 | 88 | 99 |
| 13 | 0.23 | Rb$_2$CO$_3$ 7.5 | Anthracene 5.6 | 85 | 98 |
| 14 | 0.23 | RbOH 4.0 K$_2$CO$_3$ 2.0 | Phenanthrene 5.6 | 87 | 99 |
| 15 | 0.23 | Rb$_2$CO$_3$ 7.5 | Fullerene 4.8 | 86 | 98 |
| 16 | 0.23 | Rb$_2$CO$_3$ 5.0 K$_2$CO$_3$ 2.5 | Cyanobenzene 10.0 | 90 | 99 |
| 17 | 0.23 | Rb$_2$CO$_3$ 6.0 Na$_2$CO$_3$ 1.0 KCl 0.5 | Tetracyanobenzene 4.8 | 85 | 99 |
| 18 | 0.23 | Rb$_2$CO$_3$ 7.5 | Dichloroquinone 4.8 | 80 | 98 |
| 19 | 0.23 | Rb$_2$CO$_3$ 7.5 | Tetracyanoquinone 4.8 | 81 | 99 |
| 20 | 0.45 | Rb$_2$CO$_3$ 7.5 | Quinoline 10.0 | 40 | 99 |
| Comp Example 2 | 0.23 | Rb$_2$CO$_3$ 7.5 | | 1 | 99 |

TABLE 3

| | Catalyst composition | | Product | |
|---|---|---|---|---|
| Example | Na | Salt | Aromatic compound producing a charge-transfer complex with Na | Yield (%) | Purity (%) |
|---|---|---|---|---|---|
| 21 | 0.23 | CaCO$_3$ 7.5 | Anthraquinone 4.8 | 88 | 98 |
| 22 | 0.23 | CaCO$_3$ 7.5 | Naphthalone 3.0 | 87 | 99 |
| 23 | 0.23 | MgCO$_3$ 5.0 | Anthracene 5.6 | 88 | 98 |
| 24 | 0.23 | Ca(OH)$_2$ 2.0 K$_2$CO$_3$ 2.0 | Phenanthrene 5.6 | 84 | 97 |
| 25 | 0.23 | CaCO$_3$ 6.0 Na$_2$CO$_3$ 1.0 KCl 0.5 | Tetracyanobenzene 2.4 | 82 | 98 |
| 26 | 0.23 | CaCO$_3$ 7.5 | Dichloroquinone 4.8 | 80 | 98 |
| 27 | 0.23 | CaCO$_3$ 7.5 | Tetracyanoquinone 4.8 | 80 | 99 |
| Comp. Example 3 | 0.23 | CaCO$_3$ 7.5 | | <1 | — |

Example 28

(1) Preparation of dispersion of metallic sodium 2 parts by weight of metallic sodium was charged to 100 parts of by weight of o-xylene, of which the water content was reduced to below 0.1 ppm with zeolite in advance. The metallic sodium was finely pulverized by a mechanical stirrer at 120° C. under high purity nitrogen atmosphere.

(2) Preparation of potassium type Y-zeolite carrier

A commercially available proton-type Y-zeolite was suspended in water. An aqueous solution of potassium hydroxide (1N) was added dropwise to the suspension to make the pH 12, following which the suspension was filtered and sufficiently washed, thus obtaining potassium-type Y-zeolite.

Dry boehmite alumina in an amount of 20 parts by weight, as aluminum oxide, was added to 80 parts by weight of the potassium-type Y-zeolite which was dried at 130° C. The mixture was thoroughly blended, deflocculated with the addition of 1N aqueous solution of nitric acid, and neutralized with ammonia water. The clay-like material thus obtained was molded into rings. The molded products were dried at 130° C. and calcined at 550° C. to obtain rings with an outer size of 3 mm$\phi$×3 mm.

(3) Preparation of metallic sodium-potassium type Y-zeolite carrier composite 10 parts by weight of sodium-potassium type Y-zeolite carrier prepared in (2) above, was added to 100 parts by weight of o-xylene with a water content of below 0.1 ppm. To the mixture was added 100 parts by weight of the dispersion of metallic sodium prepared in (1) above, and the resulting mixture was stirred at a high speed with a mechanical stirrer, followed by evaporation of o-xylene.

(4) Preparation of charge-transfer complex

The metallic sodium-potassium type Y-zeolite carrier composite prepared in (3) was transferred to a packing column (30 mm$\phi$×500 mm) of a distillation device equipped with this column and a 1000 ml three-necked flask, to fill out the upper 60% area of the column (an amount as catalyst: 200 ml). A coil filler (Helipack, trademark, manufactured by Nitto Han-noki Co.) was filled in the remaining part of the column.

A solution consisting of 10 parts by weight of naphthalene dissolved in 100 parts by weight of o-xylene was added dropwise from top of the column at room temperature. The addition was terminated when an amount of the solution corresponding to 1 mol of naphthalene for 1 mol of metallic sodium was added.

(5) Synthesis of 5-(o-tolyl)pentene 300 ml of o-xylene with a water content of below 0.1 ppm was charged to the three-necked flask and heated to the boiling point, thereby evaporating o-xylene vapor up to the column top and refluxing the whole amount. The system was thus stabilized.

Then, 1,3-butadiene was supplied from one of the ports of the three-necked flask at a rate of 10 ml/min.

After reacting for 3 hours in this manner, o-xylene was evaporated to obtain 5-(o-tolyl)pentene. The concentration of 5-(o-tolyl)pentene was analyzed by gas chromatography. The results shown in Table 4.

Example 29

The same experiment as in Example 28 was carried out, except that anthracene was used instead of naphthalene. The results are shown in Table 4.

Example 30

The same experiment as in Example 28 was carried out, except that in the preparation of sodium-potassium type Y-zeolite carrier prepared in Example 28 (2) potassium carbonate powder was used instead of potassium type Y-zeolite and aluminum hydroxide gel was used instead of dry boehmite alumina. The results are shown in Table 4.

TABLE 4

| Example | Concentration of 5-(o-tolyl)pentene |
|---------|-------------------------------------|
| 28      | 99.8 wt %                           |
| 29      | 99.7 wt %                           |
| 30      | 99.6 wt %                           |

Obviously, numerous modifications and variations of the present invention are possible in light of the above teachings. It is therefore to be understood that within the scope of the appended claims, the invention may be practiced otherwise than as specifically described herein.

I claim:

1. A process for manufacturing an alkenyl aromatic compound which comprises reacting an alkylbenzene and 1,3-butadiene in the presence of a catalyst composition comprising the following components (a), (b) and (c):

(a) metallic sodium, (b) at least one derivative selected from the group consisting of oxides, hydroxides and salts of potassium, oxides, hydroxides and salts of rubidium, and oxides, hydroxides and salts of an alkaline earth metal, and (c) a compound selected from the group consisting of naphthalene, anthracene, phenanthrene, pyrene, perylene, pentacene, coronene, quinone, benzoquinone, anthraquinone, cyclophane, graphite, fullerene ($C_{60}$, $C_{70}$), triphenylene, tetraphenylene: cyano-, nitro-, or halogeno-substituted compounds of these compounds; cyanobenzene, dicyanobenzene, tetracyanobenzene, nitrobenzene, trinitrobenzene, dichlorotetracyanobenzene, tetracyanoquinodimethane, dichloroquinone, and tetracyanoquinone.

2. The process according to claim 1, wherein the reaction is carried out in the presence of a composition comprising a (1) dispersion of component (a) and component (b), and (2) component (c).

3. The process according to claims 1 or 2, wherein the reaction is carried out substantially in the absence of water and oxygen.

4. The process according to claim 1, wherein component (b) is selected from the group consisting of potassium oxide, potassium hydroxide, potassium carbonate, potassium sulfate, potassium chloride, potassium aluminate, rubidium oxide, rubidium hydroxide, rubidium carbonate, rubidium sulfate, calcium oxide, calcium hydroxide, calcium carbonate, calcium sulfate, magnesium oxide, magnesium hydroxide, magnesium carbonate, and magnesium sulfate.

5. The process according to claim 1, wherein the alkylbenzene is toluene, ethylbenzene, o-xylene, m-xylene, or p-xylene.

6. The process according to claim 1, wherein the amount of component (a) used is 0.1 to 30% by weight of the total amount of component (a) and component (b).

7. The process according to claim 1, wherein the amount of component (c) used is 0.001 to 50 mols for one mol of component (a).

8. The process according to claim 1, wherein 0.01 to 50 parts by weight of said catalyst comprising components (a), (b), and (c) is used for 100 parts by weight of alkylbenzene.

9. The process according to claim 1, wherein alkylbenzene and 1,3-butadiene are reacted at a molar ratio of 1:0.001 to 1:0.5.

10. The process according to claim 1, wherein the reaction is carried out at 50° to 200° C.

* * * * *